United States Patent [19]

Meyers

[11] Patent Number: 4,803,975

[45] Date of Patent: Feb. 14, 1989

[54] ORTHOTIC DEVICE FOR CONTROLLING KNEE INSTABILITIES

[76] Inventor: Andrew H. Meyers, 31 The Birches, Roslyn Estates, N.Y. 11576

[21] Appl. No.: 32,230

[22] Filed: Mar. 31, 1987

[51] Int. Cl.$^4$ ................................................ A61F 5/00
[52] U.S. Cl. ...................................... 128/80 C; 2/22; 128/88
[58] Field of Search .................. 128/80 C, 80 F, 88, 128/87 R; 2/22, 24

[56] References Cited

U.S. PATENT DOCUMENTS

| 2,467,907 | 4/1949 | Peckham | 128/80 C |
| 3,194,233 | 7/1965 | Peckham | 128/80 C |
| 4,554,913 | 11/1985 | Womack et al. | 128/80 C |
| 4,565,190 | 1/1986 | Pirmantgen et al. | 128/80 C |

OTHER PUBLICATIONS

"The Lenox Hill Derotation Brace", Lenox Hill Brace Shop, Inc.

Primary Examiner—Edgar S. Burr
Assistant Examiner—Moshe I. Cohen
Attorney, Agent, or Firm—Sixbey, Friedman, Leedom & Ferguson

[57] ABSTRACT

An improved orthosis for correcting essentially all knee instabilities is disclosed herein. Generally, the orthosis comprises a joint structure formed from a pair of pivoting sidebars, upper and lower support assemblies, each of which includes C-shaped braces connected to the sidebars of the joint structure for supporting the pivoting portions of the sidebars over the knee joint, and a tibial retention means in the form of a Y-shaped tibial support member cantilevered from the bottom brace member of the lower support assembly for supporting the upper tibia against anterior displacements. The orthosis may further include resilient condylar pads disposed between the sidebars and the condyle regions of the knee in order to provide support against varus- and valgus-type knee instabilities. Finally, the orthosis may also include a femoral retention means in the form of a Y-shaped member cantilevered from the upper C-shaped brace member for supporting the upper femur. The upper and lower C-shaped members and their respective tibial and femoral support members are preferably integrally formed, and lined with an anti-slippage sheet material such as Neoprene ®.

17 Claims, 2 Drawing Sheets

ORTHOTIC DEVICE FOR CONTROLLING KNEE INSTABILITIES

BACKGROUND OF THE INVENTION

This invention generally relates to orthotic devices for controlling instabilities in joints, and is specifically concerned with an improved knee orthosis for providing four-point fixation against medial-lateral, anterior-posterior, and rotary knee instabilities through a mechanism that is relatively lightweight and non-bulky.

Orthotic devices for correcting knee instabilities are known in the prior art. These devices are often comprised of a mechanical joint and a pair of bracing members. The mechanical joint includes a pair of sidebars, each of which has a pivoting joint in its middle portion. The top and bottom ends of the sidebars are connected to the bracing members. The bracing members circumscribe the regions of the leg above and below the kneejoint, and support the pivoting joints of the sidebars in alignment with the kneejoint. Such prior art devices generally operate by confining the movement of the kneejoint as it bends so that unwanted motions of the lower femur and the upper tibia are eliminated or at least minimized.

Knee instabilities can take a variety of forms, including varus, valgus, rotary, anterior and posterior displacements, as well as hyperextension of the joint. Varus-type instabilities tend to bend the kneejoint outwardly, giving the leg a bow-legged orientation, while valgus instabilities tend to bend the joint inwardly, giving the leg a knock-kneed appearance. Rotary instabilities can cause femural and tibial sections of the knee to rotate excessively with respect to one another as the knee flexes. Anterior instabilities tend to separate the tibia anteriorly with respect to the femur while hyperextension-type instabilities allow the kneejoint to bend more than 180° with respect to one another.

A properly installed orthotic knee brace can counteract all of these instabilities (at least in part) by reinforcing the kneejoint as a whole, and by supporting it against such unstable movements when the kneejoint flexes. Such devices are often needed by athletes in the running sports, such as, for example, football, hockey and tennis, who have suffered injuries to their joints which make them much more prone to such unstable movements. For athletic applications, such orthotic devices should be capable of eliminating or at least minimizing all such unstable movements without impeding the proper movement of the knee in any way. Moreover, such a device should be lightweight and non-bulky so that it will neither detract from the athletic performance of the athlete by either weighing the athlete down or by rubbing against his other leg during a competitive sport. It would, of course, be desirable for the orthosis to be enclosable within a uniform. Finally, such an orthosis should provide "four-point fixation" against anterior and posterior displacements as well as varus and valgus deviations. In this context, four-point fixation means that the orthosis will resist, in at least two separate points in its structure, any shear force applied across its longitudinal axis either in the plane that the kneejoint bends (in order to prevent anterior and posterior displacements), or in the plane orthogonal thereto (in order to prevent varus-valgus instabilities). Such four-point fixation is particularly important for athletes whose kneejoints have been injured to the extent where a large amount of extra support is absolutely necessary.

While knee orthoses are known which are capable of providing four-point fixation, the mechanisms which these orthoses employ are all relatively heavy and bulky, and hence capable of impeding the performance of an athlete in a running sport. While it is possible to reduce both the size and weight of the structure used in such an orthosis, such "stripping down" of the parts of the orthosis reduces its structural strength, and hence renders it less effective in providing support against knee instabilities.

Clearly, what is needed is a knee orthosis which is capable of firmly providing four-point fixation against all knee instabilities, in a structure having less weight and less bulk than prior art knee orthoses. Ideally, such an orthosis should be simple in structure, and compact enough to be easily covered by an athletic uniform.

SUMMARY OF THE INVENTION

Briefly, the invention is an orthotic device for controlling knee instabilities that comprises a joint structure including a pair of sidebars, upper and lower support assemblies circumscribing the leg above and below the kneejoint for supporting the sidebars in alignment with the kneejoint, wherein the lower support assembly includes a tibial retention means for supporting the upper tibia against anterior displacements. The lower support assembly includes a brace member, and the tibial retention means is preferably formed from a tibial support member that is anteriorly cantilevered from the brace member. The lower support assembly may further include a strap for pulling the cantilevered tibial support member into intimate, supporting engagement with the tibia of the wearer.

The orthosis of the invention may also include at least one condyle pad positioned between one of the sidebars of the joint structure and one of the condylar regions of the knee. Preferably, this pad includes a layer of resilient material for engaging the pad against the condylar region in intimate supporting contact therewith. A second condyle pad may also be positioned between the other of the sidebars in the opposite condylar region of the knee so that both condylar regions are supported. Such a configuration renders positive support to the kneejoint against both varus and valgus instabilities.

The upper support assembly may also include a brace member, and a femur retention means in the form of a femoral support member. The femoral support member may likewise be anteriorly cantilevered to the upper brace member.

In the preferred embodiment, both the upper and lower brace members and their respective tibial and femoral support members are integrally formed from a strong, lightweight material that includes some degree of flexibility, such as anyone of a number of commercially available graphite composites. Additionally, the interiors of both the upper and lower brace members are preferably molded in the shape of the lower thigh and upper calf of the wearer in order to enhance the close engagement between the cantilevered tibial and femoral support members formed in the upper and lower brace members. Finally, each of the brace members may be lined with a non-slippage sheet material, such as foam Neoprene ®, in order to minimize slippage between the orthosis and the leg of the wearer.

BRIEF DESCRIPTION OF THE SEVERAL FIGURES

FIG. 2a is a side perspective view of the orthosis illustrated in FIG. 1a, and

FIG. 2b is a rear perspective view of the orthosis illustrated in FIG. 1a installed around the leg of a wearer.

DETAILED DESCRIPTION OF THE PREFERRED EMBODIMENT

General Overview of the Structure and Function of the Invention

Figure 1B:
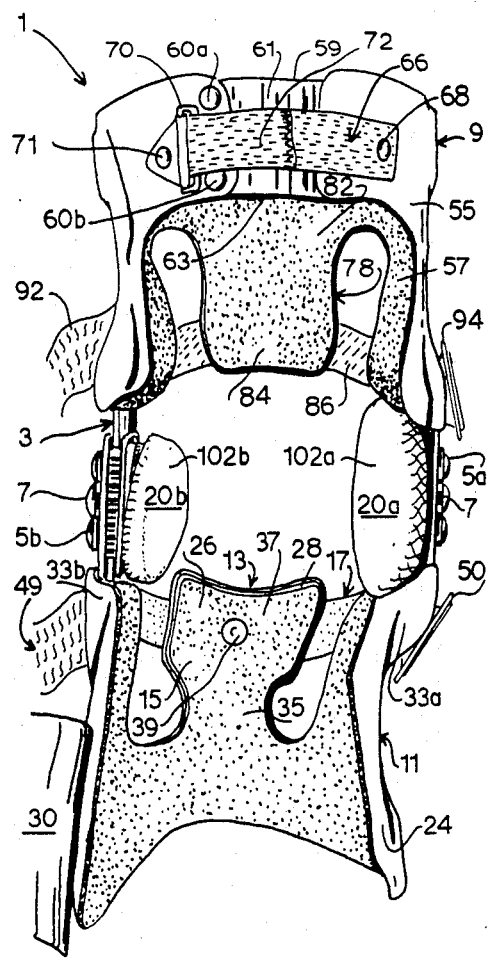
FIG. 1b is a rear perspective view of the orthosis illustrated in FIG. 1a with the leg of the wearer removed therefrom.
Figure 1A:
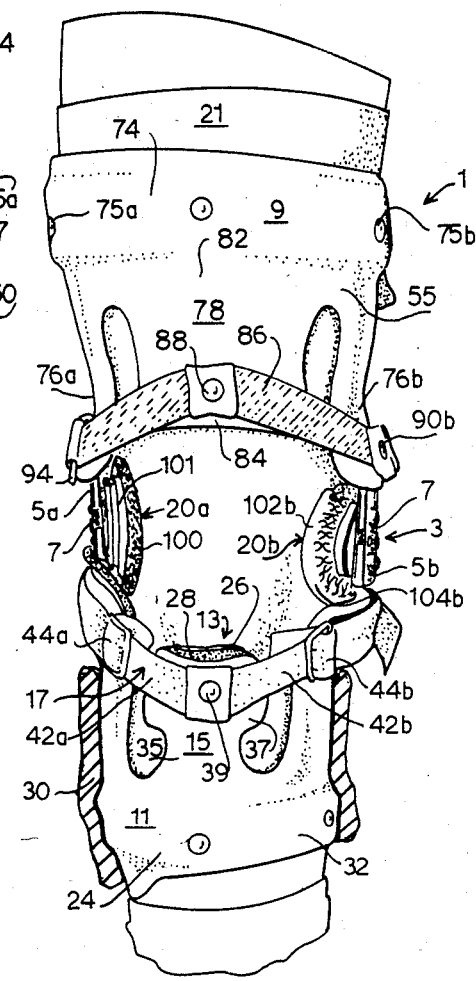
FIG. 1a is a front perspective view of the orthosis of the invention as it appears installed around the leg of a wearer.

With reference to FIGS. 1a and 1b, the knee orthosis 1 of the invention generally comprises a mechanical joint structure 3 formed from a pair of side bars 5a, 5b which include hinges 7 in their middle portions. The knee orthosis 1 further includes both an upper support assembly 9 and a lower support assembly 11 that circumscribe the portions of the leg above and below the kneejoint, respectively, and support the side bars 5a, 5b of the joint structure 3 in alignment with the kneejoint. The interiors or both the upper and lower support assemblies 9, 11 are preferably molded to conform to the shape of the leg of the wearer in order to ensure an intimate fit between the orthosis and its wearer's leg.

The lower support assembly 11 includes a tibial retainer 13 for preventing displacements of the upper portion of the tibia. The tibial retainer is generally formed from a Y-shaped, cantilevered member 15 integrally formed with the balance of the lower support assembly 11, and an anterior adjustment strap 17 for pulling the member 15 into intimate, supporting engagement against the tibia of the wearer.

Also included within the orthosis 1 are inner and other condyle pads 20a, 20b. The outer surfaces of these condyle pads 20a, 20b are mounted onto the inner sides of the hinge portions 7 of the sidebars 5a, 5b. As will be discussed in detail hereinafter, each of the condyle pad assemblies 20a, 20b includes the resilient pad formed from foam Neoprene ®. The resiliency of the Neoprene ® pads allows them to apply a uniform supporting force onto both the inner and the outer condyle regions of the knee.

The upper support assembly 9 includes a femoral retainer 78 for preventing displacements of the lower portion of the femur. Similar to the tibial retainer 13, the femoral retainer 78 is formed from a cantilevered member 80 that is integrally formed with the rest of the upper support assembly 9, and the combination of an elastic strap 86 that pulls the member 80 against the femur. A non-elastic upper posterior strap 92 cooperates with the elastic strap 86 in pulling the lower end of the femur toward the anterior portion of the wearer's leg.

To prevent the orthosis 1 from slipping out of position around the kneejoint, essentially all of the inner surfaces of the upper and lower support assemblies 9, 11 are lined with foam Neoprene ®. This foam Neoprene ® lining co-acts with a sleeve 21 of expandable material worn around the kneejoint to prevent the orthosis 1 from slipping.

Specific Description of the Orthosis of the Invention

Figures 2A, 2B:
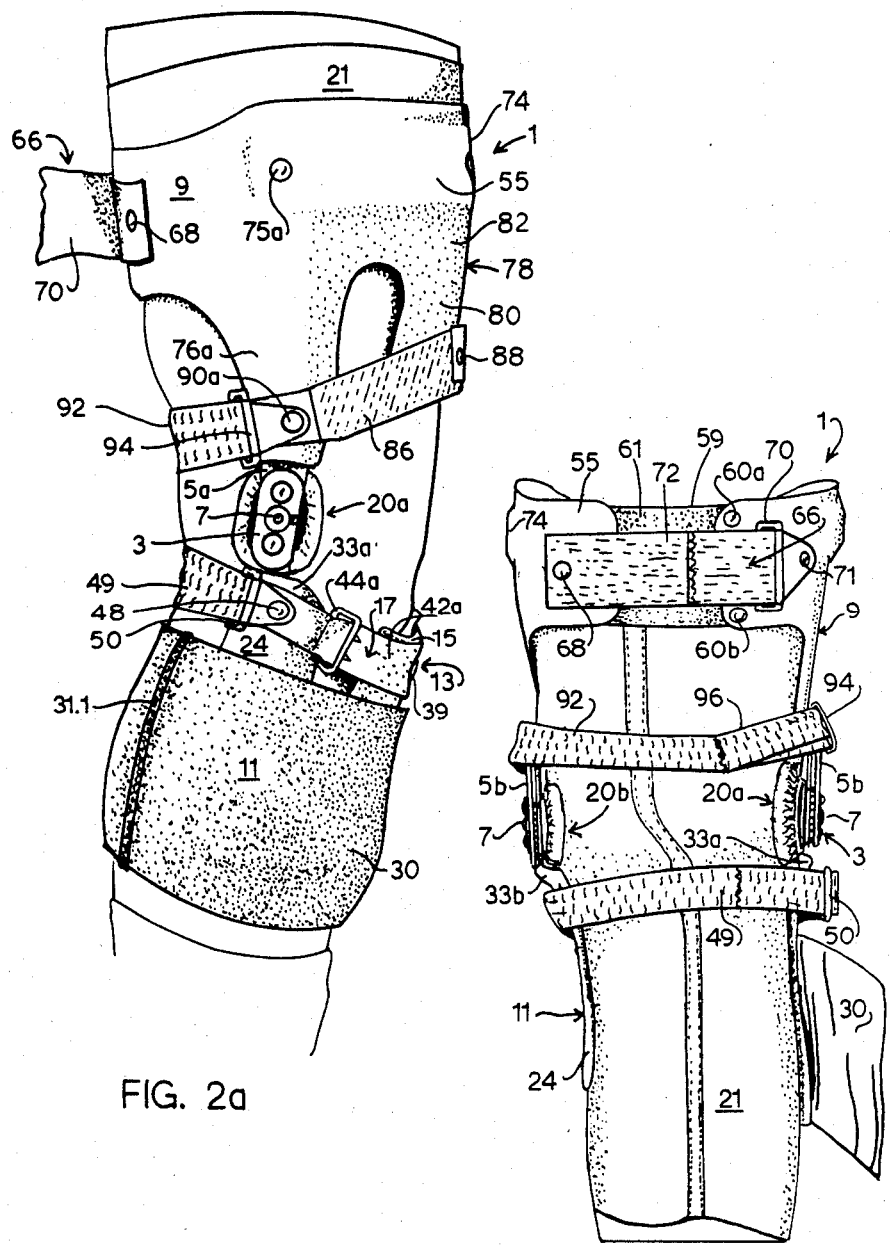

With reference again to FIGS. 1a and 1b, the lower support assembly 1 includes an integrally formed brace member 24 having a substantially C-shaped cross-section. In the preferred embodiment, the interior of the brace member 24 is molded to conform to the exterior of the anterior upper portion of the cap of the wearer. In operation, the brace member 24 surrounds only the anterior portion of the knee in the upper tibial region, as is best seen in FIG. 2a.

In its interior, the brace member 24 is lined with an anti-slippage sheet material such as foam Neoprene ®. In order to assure complete conformity between the inner surface of the Y-shaped, cantilevered member 15 of the tibial retainer 13, an additional layer 28 of resilient foam material is disposed between the outer surface of the lining 26, and the inner surface of the cantilevered member 15. On its exterior, the brace member 24 includes a flexible, resilient mounting strap that is likewise preferably formed from the foamed Neoprene ®. One end of the strap 30 is anchored to one of the side edges of the brace members 24 by means of mounting rivets 31. The free end of the strap 30 terminates in a Velcro ® fastener 31.1 so that the strap 30 may be fastened to itself after it is wrapped completely around the leg of the wearer. Around its bottom edge, the brace member 24 includes an integrally formed, lateral rib 32 formed from a band of commercially available graphite composite. Along each of its sides, the brace member 24 includes vertical corrugations 33a, 33b that meld in with this rib 32. Both the rib 32, and vertical corrugations 33a, 33b, all serve to rigidify the brace member 24. Additionally, the corrugations 33a, 33b provide longitudinal recesses along the length of the brace member 24 for receiving the bottom portions of the side bars 5a, 5b of the mechanical joint structure 3, whose bottom ends are ultimately connected to the graphite band that forms the rib 32. Sponge spacers (not shown) are provided between the bottom portions of the side bars 5a, 5b and the inner lining 26 of foam Neoprene ® so that the inner contour of the brace member 24 conforms to the upper half of the wearer in the regions around the vertical corrugations 33a, 33b.

Finally, in its anterior portion, the brace member 24 includes the previously mentioned Y-shaped, cantilevered member 15 of the tibial retainer 13. The lower portion 35 of the cantilevered member 15 defines the single leg of the Y, while the upper portion 37 defines the forks of the Y. A rivet 39 disposed through the upper portion 37 of the cantilevered member 15 anchors a pair of belts 42a, 42b over the cantilevered member 15. Each of these belts 42a, 42b includes its own separate buckle 44a, and 44b. Another rivet 48 connects the other end of belt 42a to the top of corrugation 33a, while another rivet (not shown) connects the other end of belt 42b to the top portion of the vertical corrugation 33b. Rivet 48 further serves to anchor one end of a posterior strap 49 to the upper portion of the vertical corrugation 33a, while its opposing counterpart (not shown) anchors D-ring 50 to the upper portion of vertical corrugation 33b. The free end of the posterior strap 49 includes a Velcro ® fastener 52 so that the strap may be fastened upon itself after being looped through the D-ring 50. In operation, the separate belts 42a, 42b that form the anterior adjustment strap 17 in combination with the yieldability of the relatively narrow, lower portion 35 of the Y-shaped, cantilevered member 15 allow the upper portion 37 of this member to be pulled into firm, intimate and supporting engagement against the upper tibia of the kneejoint. In particular, the separate buckles 44a, 44b of the belts 42a, 42b allow the wearer to specifically adjust the magnitude of the engagement force that the upper portion 37 of the cantilevered member 15 applies to the upper tibia, as well as the manner in which these engagement forces are distributed around the upper portion 37. In the preferred embodiment, belts 42a, 42b are formed from a strong, flexible but non-resilient sheet material, such as nylon webbing. The posterior strap 49 assists the belts 42a, 42b in pulling the member 15 into the upper tibia of the wearer by providing the side ends of the belts 42a, 42b with a point to react against. Posterior strap 49 also cooperates with the foam Neoprene ® strap 30 in firmly retaining the brace member 55 into proper position around the leg of the wearer.

With reference now to FIGS. 1a and 1b, the upper support assembly 9 likewise includes a brace member 55 that is preferably integrally formed from anyone of a number of strong, lightweight carbon-composite materials. However, instead of having a C-shaped cross section, brace member 55 has almost an O-shaped cross-section that is separated only at its posterior. In its interior, the brace member 55 includes a foam Neoprene ® lining 57 which again helps prevent slippage between the orthosis 1 and the leg of the wearer. To bridge the gap between the two ends of the brace member 55 at the posterior end of the support assembly 9, a reinforcement flap 59 is provided. One end of the reinforcement flap 59 is anchored onto one of the posterior sides of the brace member 55 by means of rivets 60a, 60b, while the other free end of the flap 59 lies flat against the inner lining 57. In the preferred embodiment, the flap 59 is formed from a layer 61 of flexible polyethylene that is lined on its interior surface with a layer 63 of foam Neoprene ®. In order to draw the two anterior ends of the brace member 55 together and thereby secure the upper support assembly 9 to the lower thigh of the wearer, a securing strap 66 is provided in the position best seen in FIGS. 1b and 2b. One end of the strap 66 is anchored to an interior end of the brace member 55 by means of a rivet 68, while the free end of the strap 66 is looped through a D-ring 70 secured to the opposing anterior end of the brace member 55 by another rivet 71. Like the previously described lower posterior strap 49, the free end of the securing strap 66 includes a Velcro ® fastener 72 in order to allow the strap 66 to be detachably fastened to itself. Disposed around the top anterior edge of the brace member 55 is an upper lateral rib 74 formed from a band of graphite composite which helps to rigidify the orthosis. Rivets 75a, 75b are provided which secure the upper ends of the side bars 5a, 5b to the graphite band that forms the lateral rib 74. Like the lower brace member 24, the upper brace member 55 includes vertical corrugations 76a, 76b for receiving the upper and middle portions of the side bars 5a, 5b. Again, sponge spacers (not shown) are disposed between the inner surfaces of these portions of the side bars 5a, 5b and the Neoprene ® lining 63 of the upper brace member 55 in order to render the interior of the upper support assembly into conformance with the shape of the lower thigh of the wearer.

The upper brace member 55 further includes femoral retainer 78 formed from a cantilevered retaining member 80 having an upper portion 82, and a lower portion 84. The femoral retainer 78 further includes an elastic strap 86 that is connected in its middle to the lower portion 84 of the cantilevered retaining member 80 by means of rivet 88, and at its ends to the lower parts of the vertical corrugations 76a, 76b by means of rivets 90a, 90b. These rivets 90a, 90b also anchor one end of an upper posterior strap 92 to the upper brace member 55, as well as a D-ring 94 to the other side of the member 55. As was the case with lower posterior strap 49, upper posterior strap 92 includes a Velcro ® fastener 96 on its free end so that the strap 92 may be detachably connected to itself after being looped through D-ring 94. The combination of the elasticity in the strap 86 and the pulling force exerted by the upper posterior strap 92 firmly engages the cantilevered retaining member 80 against the lower end of the femur when the orthosis is installed onto the leg of a wearer in the position illustrated in FIG. 2a.

In order to provide firm lateral support to both of the condyle regions on either side of the knee of the wearer, the orthosis 1 also includes the previously mentioned inner and outer condyle pads 20a, 20b. Each pad includes a foam Neoprene ® sponge pad 100 (seen in FIG. 1a) which is large and resilient enough to apply a firm yet uniform engagement force to its respective condyle region. Each of the sponge pads 100 is glued on its outside surface to a plastic retaining cap (not shown) that is in turn mounted on the inside of each of the sidebars 5a, 5b. To prevent the foam Neoprene ® pads 100 of each of the condyle pads 20a, 20b from frictional engagement against the exterior sleeve 21 of material wrapped around the leg of the wearer, each of the pads 100 is covered by a flannel case 102a, 102b. The outer edges of each of these cases 102a, 102b terminate in an elastic strap 104a, 104b so that the case may be mounted over its respective pad 100 in much the same way that a conventional shower cap fits over the head of a bather. In operation, each of the sponge pads 100 that forms the largest part of the condyle pad assemblies 20a, 20b reacts off the inner side of its respective side bar 5a, 5b to apply an intimate, firm and uniform supporting force to its respective condyle region of the knee. Moreover, because the side bars 5a, 5b are indirectly connected to one another by way of the upper and lower brace members 24, 55, the pad assemblies 20a, 20b tend to help prevent the orthosis 1 from slipping out of position around the knee of the wearer by applying a constant "centering" force between the side bars 5a, 5b, and the condyle regions of the knee of the wearer.

I claim:

1. An orthotic device for controlling knee instabilities, comprising:
    (a) a joint structure including a pair of sidebars;
    (b) upper and lower support assemblies for circumscribing the leg above and below the kneejoint and connected to the joint structure for supporting the sidebars over the sides of the kneejoint;
    (c) at least one condyle pad positioned between one of said sidebars of the joint structure and one of the condylar regions of the knee, wherein said pad includes a layer of resilient material for engaging said pad against said condylar region in intimate supporting contact therewith, and
    (d) a brace member forming a portion of said lower support assembly having a tibial retention means including a tibial support member that is cantilevered from said brace member, and a strap means for maintaining the tibial support member in intimate supporting contact against an upper portion of the tibia for supporting the upper portion of the tibia against anterior displacements.

2. The device of claim 1, wherein said strap circumscribes the brace member over the cantilevered support member of the retention means.

3. The device of claim 1, wherein a second condyle pad is positioned between the other of said sidebars and the opposite condylar region of the knee,
and said second pad having a layer of resilient material for engaging the second pad against the opposite condylar region in intimate supporting contact therewith, so that both condylar regions of the knee are supported.

4. The device of claim 1, wherein said upper support assembly includes a brace member whose interior conforms to the external shape of the lower thigh that it circumscribes.

5. The device of claim 1, wherein said condyle pad is mounted onto the sidebar it is positioned adjacent to.

6. An orthotic device for controlling knee instabilities, comprising:
(a) a joint structure including a pair of sidebars having pivotable joints in their middle portions,
(b) upper and lower support assemblies for circumscribing the leg above and below the kneejoint and connected to the upper and lower ends of the sidebars for supporting the sidebars over the sides of the kneejoint, and a condyle pad positioned between each of said sidebars and each of the condylar regions of the knee, each of said pads including a layer of resilient material for engaging its respective pad against its respective condylar region, and
(c) a brace member forming a portion of said lower support assembly having a tibial retention means including a tibial support member that is cantilevered from the brace member, and a strap means for maintaining the support member in intimate supporting contact against an upper portion of the tibia for supporting the upper tibia against anterior displacement.

7. The device of claim 6, wherein said strap means circumscribes the brace member over the cantilevered support member of the tibial retention means.

8. The device of claim 6, wherein the layer of resilient material of each of the condyle pads cooperates with the sidebars of the joint strucutre so that each pad is maintained against its respective condyle region with substantially the same supporting force.

9. The device of claim 6, wherein the upper support assembly includes a brace member, and a femur retention means that includes a femoral support member that is cantilevered from the brace member, and a strap means for maintaining the support member in intimate, supporting contact against the lower femur.

10. The device of claim 6, wherein the upper support assembly includes an upper brace member which is mountable onto a portion of a leg by a strap means, and is lined with an antislippage sheet material.

11. An orthotic device for controlling knee instabilities, comprising:
(a) a joint structure including a pair of sidebars, each of which has a pivotable joint in its middle portion;
(b) upper and lower support assemblies for circumscribing the leg above and below the kneejoint and connected to the upper and lower ends of the sidebars for supporting the sidebars over the sides of the kneejoint, wherein said lower support assembly has a C-shaped brace member that surrounds the anterior portion of the upper calf, and
(c) a tibial retention means which includes a Y-shaped member that is cantilevered to the brace member, and a strap means for engaging the Y-shaped member into intimate supporting contact with the upper tibia to prevent anterior tibial displacements.

12. The device of claim 11, including a condyle pad positioned between one of said sidebars of the joint structure and one of the condylar regions of the knee, wherein said pad includes a layer of resilient material for engaging said pad against said condylar region in intimate supporting contact therewith.

13. The device of claim 12, wherein a second condyle pad is positioned between the other of said sidebars and the opposite condylar region of the knee, said second pad having a layer of resilient material for engaging the second pad against the opposite condylar region in intimate, supporting contact therewith so that both condylar regions of the knee are supported.

14. The device of claim 11, wherein the upper support assembly includes a brace member, and a femur retention means that includes a femoral support member that is cantilevered from the brace member, an a strap means for maintaining the support member in intimate, supporting contact against the lower femur.

15. The device of claim 13, wherein the layer of resilient material of each of the condyle pads cooperates with the sidebars of the joint structure so that each pad is maintained against its respective condyle region with substantially the same supporting force.

16. The device of claim 11, wherein the upper support assembly includes a brace member, and a femur retention means that includes a femoral support member that is cantilevered from the brace member, and a strap means for maintaining the support member in intimate, supporting contact against the lower femur.

17. The device of claim 11, wherein the uper assembly also includes a brace member, and wherein the interiors of both the upper and lower brace members conform to the exterior shape of the lower thigh and upper calf of the wearer, and are substantially lined with an anti-slippage material to maintain the orthosis in proper position on the wearer's leg.

* * * * *